US012496405B2

(12) United States Patent
Maxfield

(10) Patent No.: US 12,496,405 B2
(45) Date of Patent: Dec. 16, 2025

(54) MEDICAMENT DELIVERY DEVICE WITH A LOCKING MECHANISM

(71) Applicant: SHL MEDICAL AG, Zug (CH)

(72) Inventor: Brian Maxfield, Delray Beach, FL (US)

(73) Assignee: SHL Medical AG, Zug (CH)

( * ) Notice: Subject to any disclaimer, the term of this patent is extended or adjusted under 35 U.S.C. 154(b) by 729 days.

(21) Appl. No.: 17/798,641

(22) PCT Filed: Dec. 21, 2020

(86) PCT No.: PCT/EP2020/087452

§ 371 (c)(1),
(2) Date: Aug. 10, 2022

(87) PCT Pub. No.: WO2021/185478

PCT Pub. Date: Sep. 23, 2021

(65) Prior Publication Data

US 2023/0082704 A1 Mar. 16, 2023

Related U.S. Application Data

(60) Provisional application No. 62/990,463, filed on Mar. 17, 2020.

(30) Foreign Application Priority Data

May 22, 2020 (EP) .................................... 20176034

(51) Int. Cl.
*A61M 5/315* (2006.01)
*A61M 5/20* (2006.01)

(52) U.S. Cl.
CPC ...... *A61M 5/31511* (2013.01); *A61M 5/3158* (2013.01); *A61M 2005/208* (2013.01);
(Continued)

(58) Field of Classification Search
CPC ...... A61M 5/178; A61M 5/20; A61M 5/3158; A61M 2005/2026; A61M 2005/2073; A61M 2005/208
See application file for complete search history.

(56) References Cited

U.S. PATENT DOCUMENTS 7,785,292 B2 8/2010 Harrison
2005/0101919 A1* 5/2005 Brunnberg ............ A61M 5/326 604/197
(Continued)

FOREIGN PATENT DOCUMENTS

EP 2781230 B1 8/2019
EP 2305335 B1 12/2020
(Continued)

OTHER PUBLICATIONS

International Search Report and Written Opinion for Int. App. No. PCT/EP2020/087452, mailed Feb. 11, 2021.

*Primary Examiner* — Kami A Bosworth
(74) *Attorney, Agent, or Firm* — McDonnell Boehnen Hulbert & Berghoff LLP

(57) ABSTRACT

A dose delivery mechanism and a medicament delivery device are presented having a housing holding a medicament container and a power unit, where the power unit has a plunger rod, a drive spring, operably arranged to act on the plunger rod and on the medicament container. A locking ring is operatively engaged with an actuator having a holding ledge that can releasably hold the plunger rod with the drive spring in a tensioned state, and with an actuator sleeve to form a lock that prevents axially movement of the actuator after dose delivery. The locking ring also cooperates with the actuator to generate an end-of-dose delivery signal. An activator is directly engaged with the actuator to provide a well-defined activation point.

20 Claims, 13 Drawing Sheets

(52) U.S. Cl.
CPC . *A61M 2205/273* (2013.01); *A61M 2205/581* (2013.01); *A61M 2205/582* (2013.01)

(56) References Cited

U.S. PATENT DOCUMENTS

| | | | | |
|---|---|---|---|---|
| 2006/0189938 | A1* | 8/2006 | Hommann .......... | A61M 5/2033 604/137 |
| 2009/0312705 | A1* | 12/2009 | Grunhut ................ | A61M 5/326 604/110 |
| 2010/0298780 | A1* | 11/2010 | Laiosa ................ | A61M 5/2033 604/198 |
| 2013/0035642 | A1* | 2/2013 | Daniel ................ | A61M 5/3158 604/189 |
| 2018/0185583 | A1* | 7/2018 | Hogdahl ............... | A61M 5/326 |
| 2019/0290849 | A1 | 9/2019 | Hirschel et al. | |

FOREIGN PATENT DOCUMENTS

| | | | |
|---|---|---|---|
| WO | 2011/005177 | A1 | 1/2011 |
| WO | 2011/043714 | A1 | 4/2011 |
| WO | 2014/005807 | A1 | 1/2014 |
| WO | 2017/005518 | A1 | 1/2017 |
| WO | 2017/220311 | A1 | 12/2017 |

* cited by examiner

MEDICAMENT DELIVERY DEVICE WITH A LOCKING MECHANISM

CROSS REFERENCE TO RELATED APPLICATIONS

The present application is a U.S. National Phase Application pursuant to 35 U.S.C. § 371 of International Application No. PCT/EP2020/087452 filed Dec. 21, 2020, which claims priority to U.S. Provisional Patent Application No. 62/990,463 filed Mar. 17, 2020, and European Patent Application No. 20176034.5 filed May 22, 2020. The entire disclosure contents of these applications are herewith incorporated by reference into the present application.

TECHNICAL AREA

The present disclosure relates to a dose delivery mechanism for use in a medicament delivery device that uses a locking mechanism to generate an end-of-dose delivery signal and also to prevent axial retraction of a delivery member guard.

BACKGROUND

A large number of medicament delivery devices for self-medication have been developed during the years, where many have a high degree of automatic functions and features in order to facilitate the use of the medicament delivery device, especially for inexperienced users.

One device that has gained a lot of attention on the market for its functionality is disclosed in the document WO 2011/005177 A1. The device disclosed therein has a number of automatic features like auto-penetration, auto-injection and automatic covering of the injection needle after removal of the medicament delivery device from the dose delivery site.

Even though working very well, such medicament delivery devices have a number of mechanical components that provides an increased complexity regarding interaction between the individual components that can lead to frictional issues during device use. Likewise, a large number of components can lead to device assembly complexity and thus increased manufacturing costs due to the number of components. It would be advantageous to efficiently utilize the mechanical components to perform more than a single function and to design the components to minimize friction force during use of the delivery device. Also, having components that directly engage, as opposed to indirectly engage, other components to cause an action results in well-defined activation points, i.e. instead of using a number of components that are indirectly connected to form a complex mechanism.

SUMMARY

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

One aim of the present disclosure is to remedy the drawbacks of state-of-the-art medicament delivery devices and to provide a solution with a good functionality and to minimize complex arrangements of mechanical components, while at the same time reducing frictional forces. This aim is solved by medicament delivery devices incorporating the various embodiments disclosed herein. More specifically, incorporation of one of the possible locking mechanisms utilizing a ring of the present disclosure will allow for direct connection between an activator, for example a user operated button, and an activator that initiates medicament delivery such that the user of the delivery device will experience a well-defined activation point immediately prior to the commencement of medicament dose delivery.

One possible dose delivery mechanism of the present disclosure that can be incorporated into a medicament delivery device design includes a plunger rod having a groove located on an outside surface of the plunger rod and an actuator having a holding ledge that is engaged with the groove such that the plunger rod is held in a first axial position and where disengagement of the holding ledge from the groove allows the plunger rod to move to a second axial position. An actuator sleeve is also part of the delivery mechanism, where the actuator is biased proximally by a sleeve spring. The actuator sleeve is movable in both a distal and proximal direction and has a flexible finger. There is also an activator movable in a proximal direction and directly engaged with the actuator such that axial movement of the activator moves the actuator proximally relative to the actuator sleeve. A locking ring is present that is slidably engaged and rotationally fixed with an outside surface of the actuator and is also engaged with the sleeve spring. The locking ring has a proximally extending first leg that abuts a flexible arm on the actuator when the plunger rod is in the second axial position. This abutment forms a first locking mechanism.

In a preferred configuration of a dose delivery mechanism of the present disclosure, the activator can be directly engaged with a distal end of the actuator and having a distal end surface of the locking ring that can be engaged with a distal end of the sleeve spring. The relative movement between the first leg and the flexible arm to form the first locking mechanism can generate an end of medicament notification, i.e., end-of-dose delivery, through a tactile or audible signal that is communicated to a user of the delivery device. The locking ring according to the present disclosure can have a proximally extending second leg that abuts the flexible finger on the actuator sleeve after the plunger rod has moved to the second axial position to form a second locking mechanism or axial lock that prevents axial movement of the actuator sleeve in a distal direction. This second locking mechanism also prevents distal movement of a delivery member guard so as to prevent exposure of the used delivery member, which in the case of an injection needle can eliminated accidental needle sticks. Further, the inside surface of locking ring can have a first set of splines that are slidably engaged with a second set of splines on the outside surface of the actuator that prevent relative rotation of the locking ring relative to the actuator and an outer housing of the medicament delivery device.

In yet another possible embodiment of the dose delivery mechanism of the present disclosure is the plunger rod, preferably one that is hollow, and a drive spring operatively connected to the plunger rod. In the case of a hollow plunger rod, the drive spring is located inside the plunger rod. The dose delivery mechanism can further include a guide rod positioned inside of the drive spring, where the guide rod has a distal end portion configured to slidably engage a distal end of the actuator such that the guide rod is rotationally fixed relative to the actuator. Preferably the drive spring is biased between the distal end portion of the guide rod and a proximal interior wall of the plunger rod when the plunger rod is in the first axial position.

A medicament delivery guard can also be axially fixed to the actuator sleeve such that both components move together proximally and distally. The medicament delivery guard may be included in the dose delivery mechanism that is configured to have a first position, a second position and a third position relative to the activator. The flexible finger of the actuator sleeve can have a radial inward directed protrusion that abuts a proximal facing end surface of the first leg when the plunger rod is in the second axial position such that the medicament delivery guard is prevented from axial movement in the distal direction relative to the actuator. This is the above mentioned second locking mechanism.

The dose delivery mechanism can also be configured to include a holding element that is releasably engaged with the groove in the outside surface of the plunger rod when the plunger rod is in the first axial position and disengaged from the groove when the plunger rod is in the second axial position. A medicament container holder can be axially fixed to the holding element and slidably positioned inside the medicament delivery guard. In another possible design, the holding ledge of the actuator is located at a proximal end of a tongue that is biased radially outward relative to the plunger rod. The actuator sleeve can also be arranged slidable in relation to the actuator. The holding ledge may be located at a proximal end of the tongue. The axial movement of the medicament delivery guard is preferably in a distal direction that causes the actuator sleeve to move distally to an activation state. An axial movement of the activator in a proximal direction, for example, as a result of the user pushing the activator that can be configured and shaped as a button, when the actuator sleeve is in the activation state, can cause the actuator to move relative to the actuator sleeve such that the holding ledge will disengage from the groove. This will initiate an automatic sequence that will result in the dispensing of medicament from the dose delivery device.

Yet another embodiment of the present disclosure would be directed to a complete medicament delivery device that includes one of the dose delivery mechanisms as described above that is positioned within an outer housing, i.e., a housing, of the medicament delivery device. Such a delivery device preferably contains a medicament container operatively connected to the dose delivery mechanism and a medicament delivery member connected to the medicament container.

In another embodiment, the actuator is tubular and the actuator sleeve is tubular, and the actuator is slidably and coaxially arranged to the actuator sleeve.

In another embodiment, the dose delivery mechanism comprises a medicament container comprising a stopper. In another embodiment, the plunger rod is arranged to act on the stopper during use of the dose delivery mechanism. In another embodiment, the activator is a push button.

In another embodiment, the holding ledge is an annular inwardly directed ledge. In another embodiment, the holding ledge is arranged in the groove prior to use.

In another embodiment, the locking ring comprises an end cap. In another embodiment, a distal end portion of a drive spring is in the end cap.

Another embodiment of the present disclosure is directed to a dose delivery mechanism as described above wherein a distal end surface of the locking ring is engaged with a distal end of the sleeve spring and/or wherein the activator is directly engaged with a distal end of the actuator.

A medicament delivery device of the present disclosure can have a dose delivery mechanism according to any of the embodiments above. In particular, the medicament delivery device may comprise a dose delivery mechanism according to any of the embodiments above positioned within a housing of the medicament delivery device, wherein the medicament delivery device comprises a medicament container operatively connected to the dose delivery mechanism and a medicament delivery member connected to the medicament container.

In another embodiment, the medicament delivery device may comprise an outer housing, arranged to accommodate a medicament container as well as a power unit arranged inside the outer housing, where the medicament container is arranged with a movable stopper. The power unit can contain one of the above-described dose delivery mechanisms. Preferably the power unit may comprise a plunger rod, a drive spring operably arranged to act on the plunger rod wherein the plunger rod may be operably arranged to act on the medicament container, more specifically to cause axial movement of the stopper in a proximal direction to dispense medicament through a delivery member, e.g., an injection needle, that can be attached to the proximal end of the medicament container. Further an actuator may be arranged slidably around the plunger rod such that one or more holding element can releasably engage and hold the plunger rod with the drive spring in a pre-tensioned state such that a basing force is exerted on an inside proximal end surface of the hollow plunger rod. A locking ring and a actuator sleeve can also be arranged around the actuator.

According to a favourable solution, the medicament delivery device may further comprise a medicament delivery member guard slidably movable axially within the outer housing and arranged to act on the actuator sleeve for setting the holding elements with the actuator sleeve in a first activation state. Also, an activator button may be arranged to be manually operated by a user of the device and which is directly connected to the actuator such that the proximal movement of the activator button places the holding elements in a second activation state activator such that the plunger rod is released when both activation states are set. The locking ring can provide the two locking mechanisms described above.

These and other aspects of, and advantages with, the present disclosure will become apparent from the following detailed description of the disclosure and from the accompanying drawings.

BRIEF DESCRIPTION OF DRAWINGS

In the following detailed description of the present disclosure, reference will be made to the accompanying drawings, of which

DETAILED DESCRIPTION

Figure 1:
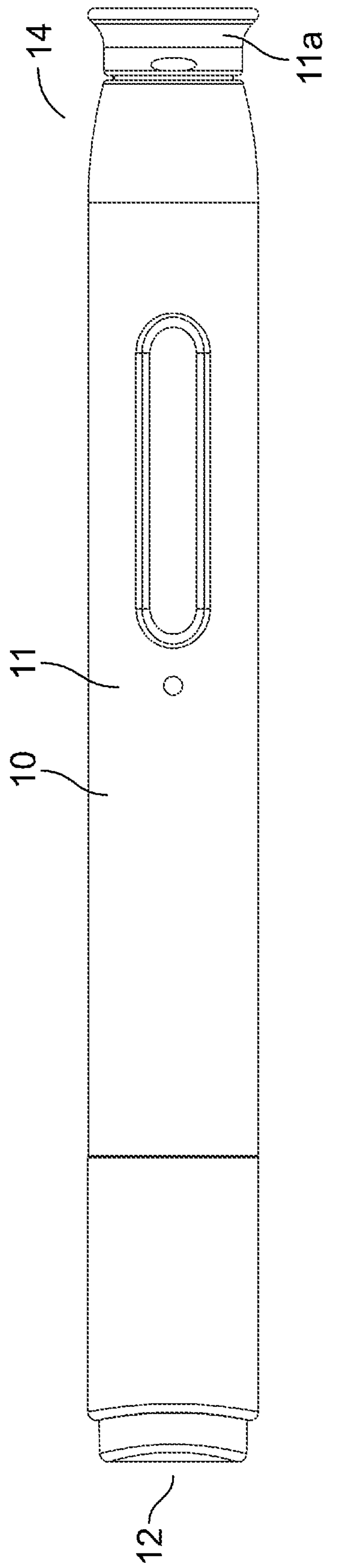
FIG. 1 shows one possible configuration of a complete medicament delivery device configured as an auto-injector that contains the locking mechanism of the instant disclosure.
Figure 2:
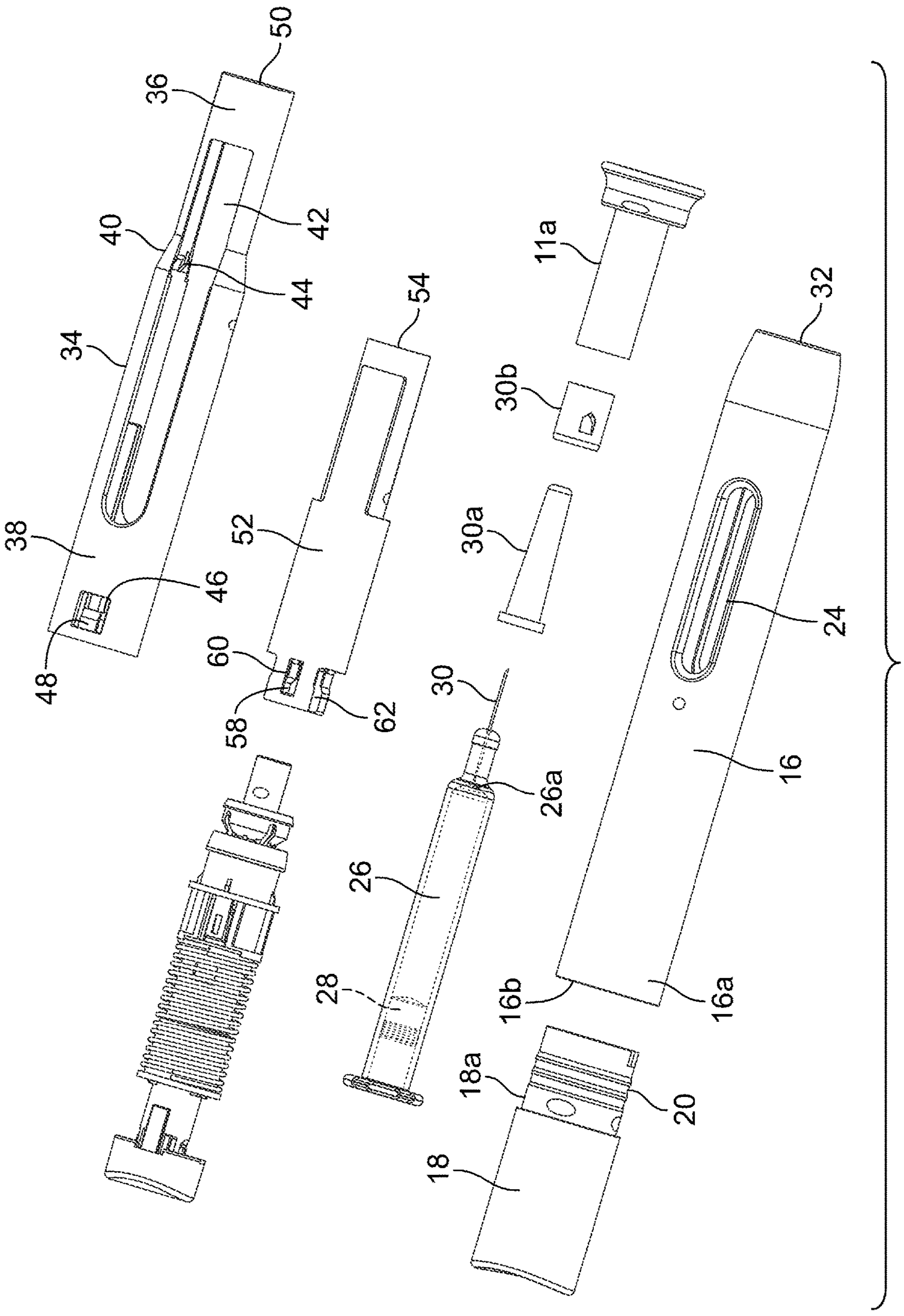
FIG. 2 shows an exploded view of the medicament delivery device of FIG. 1.

FIG. 1 shows one possible example of an embodiment of a generally elongated medicament delivery device 10 of the present disclosure having a distal end 12 and a proximal end 14. FIG. 2 shows an exploded view of medicament delivery device 10 having an elongated outer housing 11 comprising a proximal housing part 16 and a distal housing part 18. A protective cap 11*a* is positioned on the proximal end 14 to protect and cover delivery member 30. The distal end 16*a* of the proximal housing part 16 is arranged with one part of a connector 16*b*, such as annular recesses, e.g. on its inner surface adapted to interface with corresponding and cooperating connector engagement means 20 on the proximal outer surface 18*a* of the distal housing part 18.

The proximal housing part 16 is arranged with elongated openings 24 for viewing a medicament container 26, FIG. 2. The medicament container 26 is arranged with a movable stopper 28 and a medicament delivery member 30. In the embodiment shown, the medicament delivery member 30 is an injection needle that is integrated in the medicament container 26, but it is to be understood that the medicament delivery member 30 may be an attachable member wherein the attachment elements may be threads, snap fits, bayonet fittings or Luer-Lok type couplings, just to mention a few. Covering, protecting and maintaining the sterility of member 30 is a flexible shield 30*a*, e.g. needle shield, that is covered and operatively connected by shield remover 30*b* which is axially fixed to protective cap 11*a* such that the removal of cap 11*a* from engagement with the proximal end of housing 11 will remove the flexible shield 30*a* from member 30.

The proximal housing part 16 is further arranged with a central passage 32 through which a medicament delivery member guard 34 can extend. The medicament delivery member guard 34 comprises a first proximal part 36 having a certain diameter and a second distal part 38 having a diameter larger than the proximal part, where these parts are joined by an intermediate conical part 40, FIG. 2. Two elongated slits 42 are arranged along the medicament delivery member guard 34, on opposite sides thereof, for viewing the medicament container 26. On an inner surface of the conical part 40 a ledge 44 is arranged.

At the distal end of the medicament delivery member guard 34 there can be two openings 46 that are arranged opposite each other, where each opening 46 is arranged with a proximally directed, somewhat inwardly projecting, flexible, tongue 48, FIG. 2. The medicament delivery member guard 34 is further arranged with a central opening 50 at its proximal end, through which the medicament delivery member 30 may protrude during dose delivery.

A generally tubular medicament container holder 52 is slidably and coaxially arranged inside the medicament delivery member guard 34. The proximal part of the medicament container holder 52 is arranged with a central passage 54 through which the medicament delivery member 30 may protrude. The central passage 54 can be arranged with an annular support surface that cooperates with a neck portion 26*a* of the medicament container 26 providing a support and reference position for the medicament container 26. The distal end of the medicament container holder 52 is arranged with two distally extending tongues 58, where each tongue is arranged with an opening 60 and an inwardly directed ledge 62 on the distal edge of each opening, FIG. 2.

Figure 3:
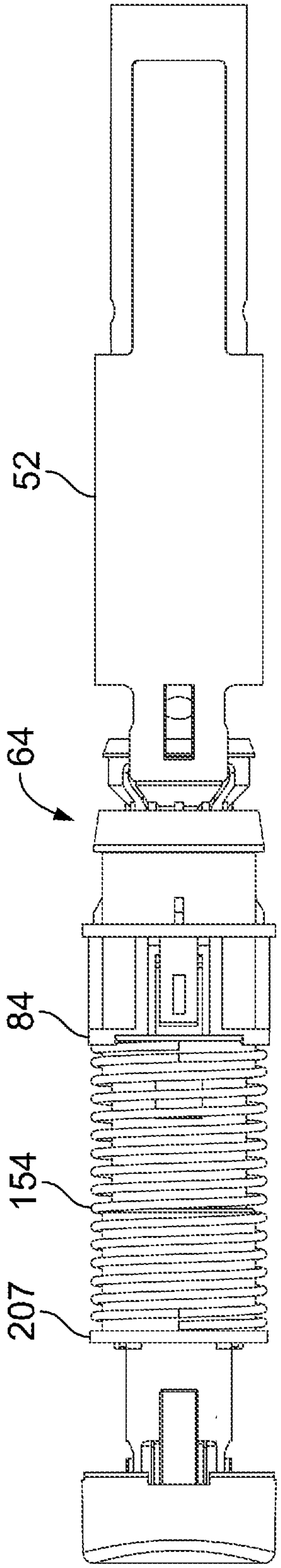
FIG. 3 shows a perspective view of one possible power unit of the medicament delivery device of FIG. 1.
Figure 4:
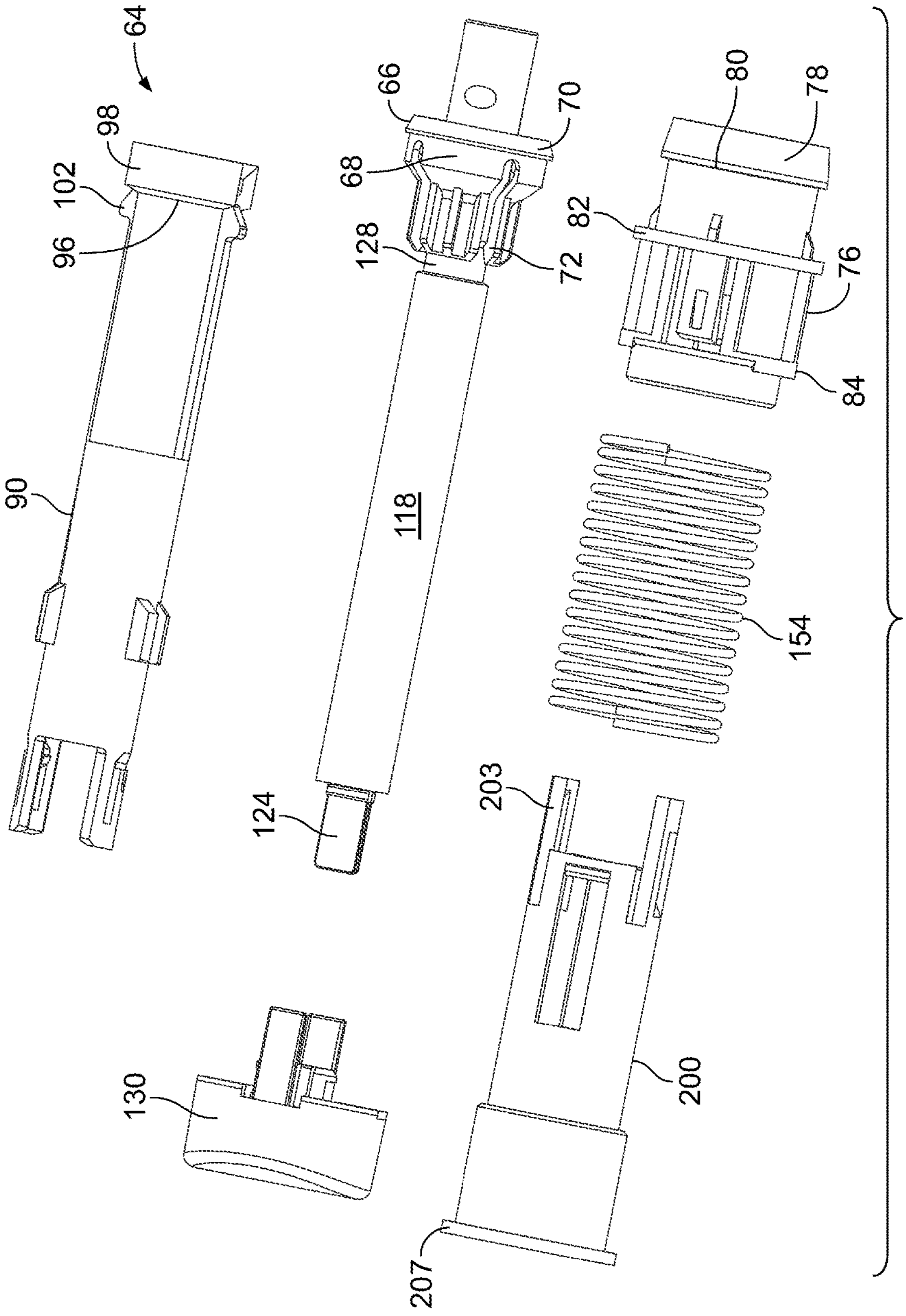
FIG. 4 shows an exploded view of the power unit of FIG. 3.

The medicament delivery device further comprises a power unit 64, FIGS. 3 & 4. The power unit 64 has a holding element 66 that is designed and configured as a ring-shaped body 68 having an annular ledge 70 arranged around its circumference and a number of flexible tongues 72 directed towards the distal end of the delivery device. Each tongue 72 is arranged with radially inwardly directed ledges that are configured to engage plunger rod 118 in groove 128. The holding element 66 is intended to interact with the container holder 52. The power unit 64 further has a locking ring 200 and an actuator sleeve 76, which is slidably and coaxially arranged to the inside surface of housing 11 and connected to the medicament delivery member guard 34 such that both are axially fix to one another and both are rotationally fixed relative to the outer housing.

The actuator sleeve 76 has a tubular shape and comprises a proximal end with a conical part 78 ending in a ledge 80 on its outer surface. At a distance from the ledge 80, a first annular ring 82 is arranged on the outer surface. A second annular ring 84 is also arranged a further distance from the ledge 80, which provides an engagement surface or biasing stop for the proximal end of sleeve spring 154. One or more protrusions 89 configured to act as proximally directed ledges are arranged on the inner surface of the proximal end of actuator sleeve 76. The actuator sleeve at its distal end is further arranged with a flexible finger 79 having a radially inward directed protrusion 79*a* configured to operatively engage with a terminal end surface 202 of the second leg 206 of the locking ring 200 (see FIG. 9). This abutment between 202 and 79*a* will prevent axial movement of the guard 34 and actuator sleeve 76 in the distal direction.

Figure 7A:
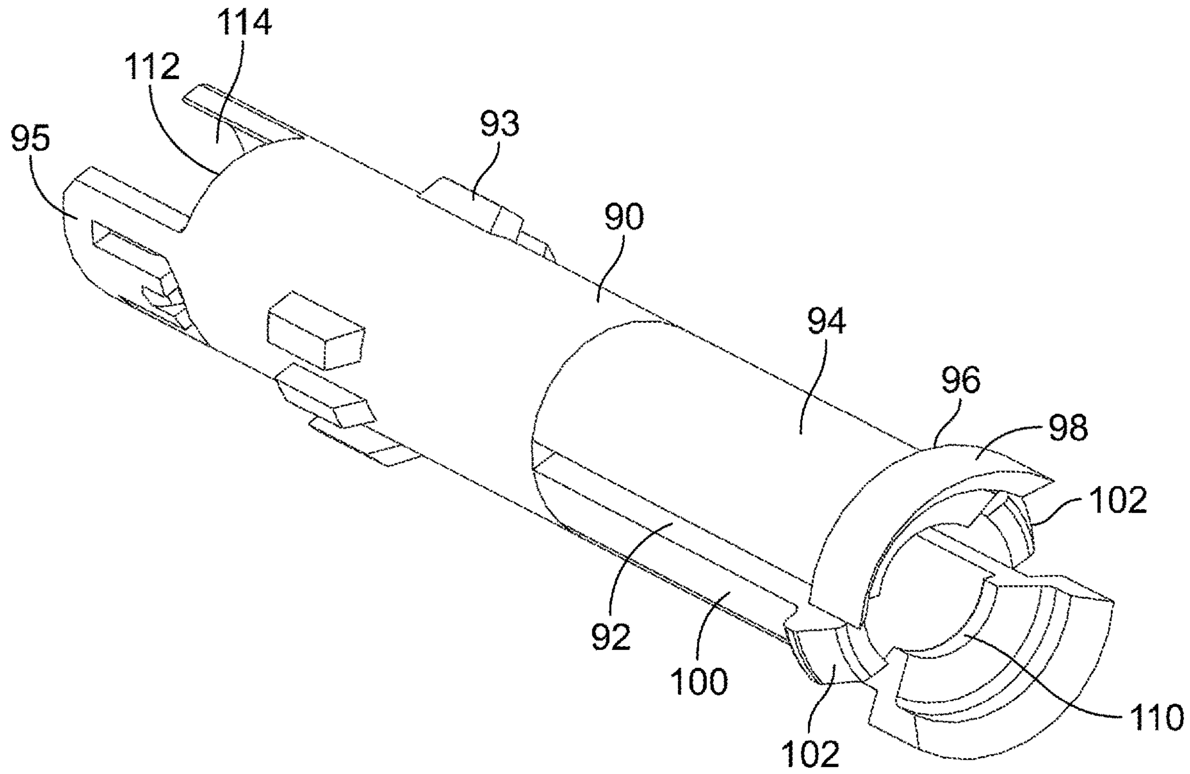
FIGS. 7A and 7B show different perspective views of the one possible design of the actuator sleeve of the present disclosure.
Figure 7B:
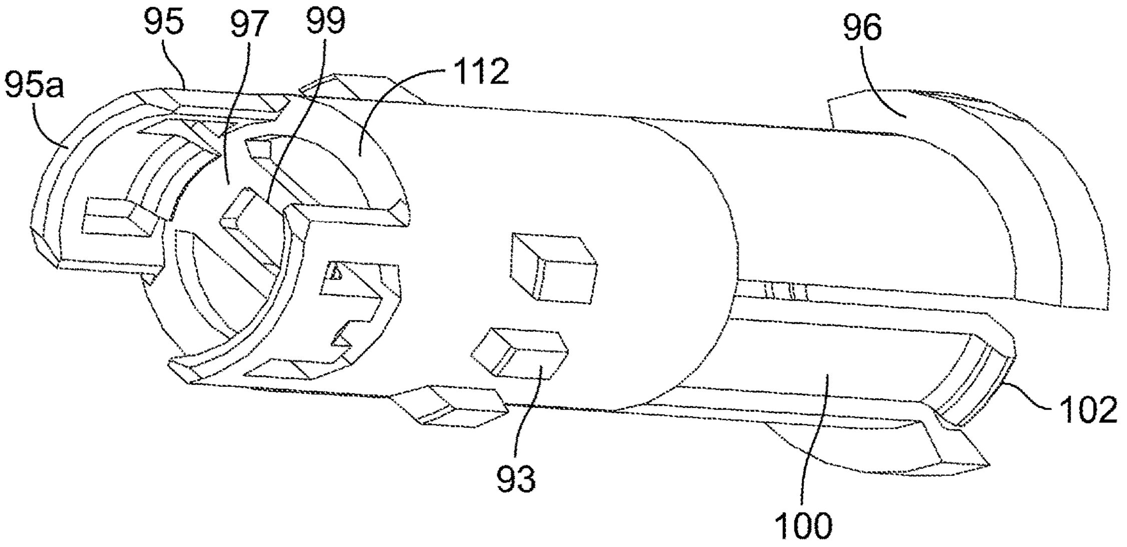
Figure 8:
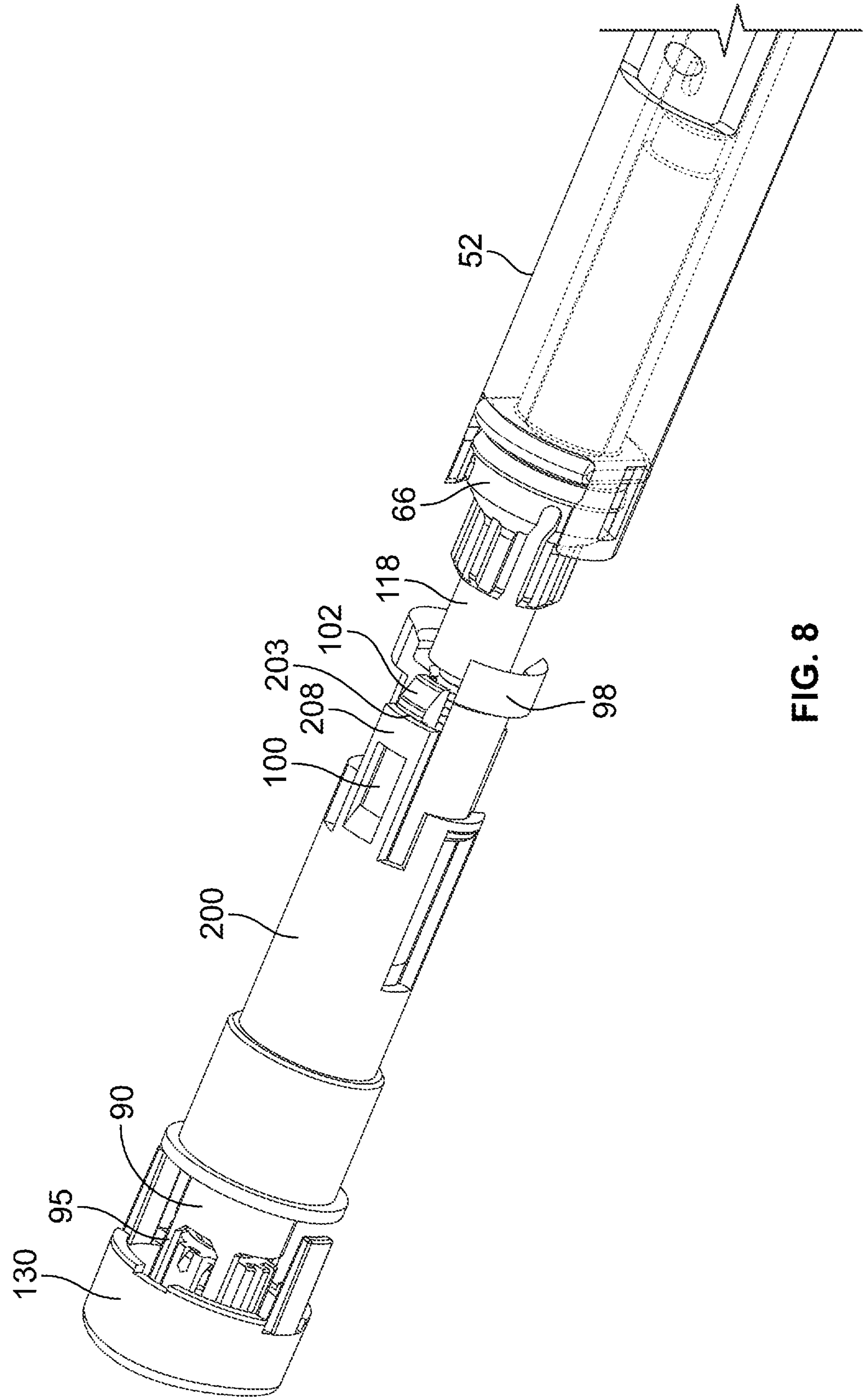
FIG. 8 shows the engagement of the locking ring of FIG. 5 with the actuator of FIG. 7A at an end of dose delivery position.

A generally tubular actuator 90, FIGS. 7A & 7B, is slidably and coaxially arranged to the actuator sleeve 76. The actuator 90 has a number of longitudinally directed cut-outs 92 that are arranged at the proximal end of the actuator 90 so as to form flexible tongues 94 and flexible arms 100 that terminate proximally with outward facing locking nibs 102. These locking nibs will engage a terminal end 203 of a proximally extending first leg 208 of locking ring 200 (see FIG. 8) forming the first locking mechanism described above. The proximal end of each flexible tongue 94 has an inclined transition surface 96 which meets with a band-shaped part 98 with enlarged diameter. On the inner surface adjacent the transition surface 96 an annular inwardly directed ledge 110 is arranged, FIG. 7A. The tongues 94 with the ledges 110 form holding ledges as will be described.

Figure 5:
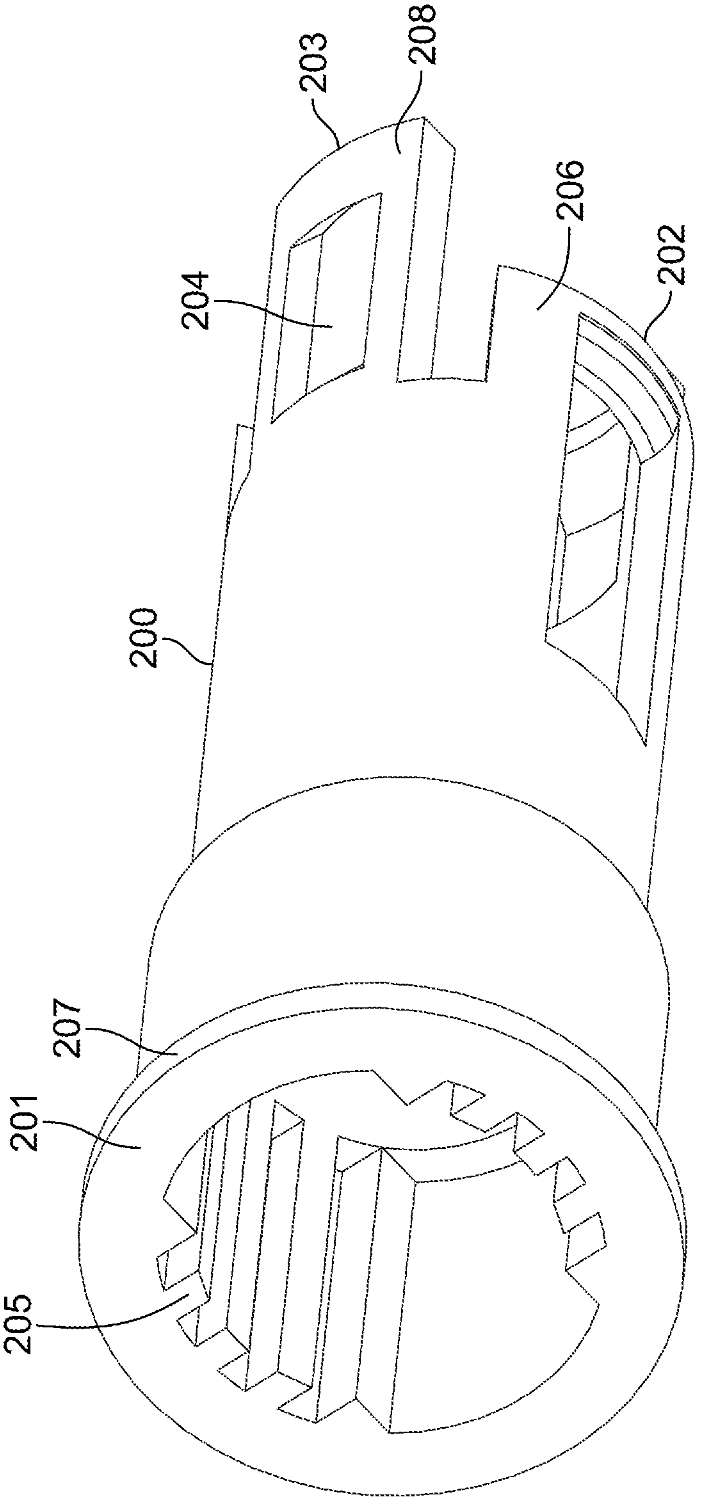
FIG. 5 shows a perspective view of one possible design of the locking ring of the present disclosure.
Figure 6A:
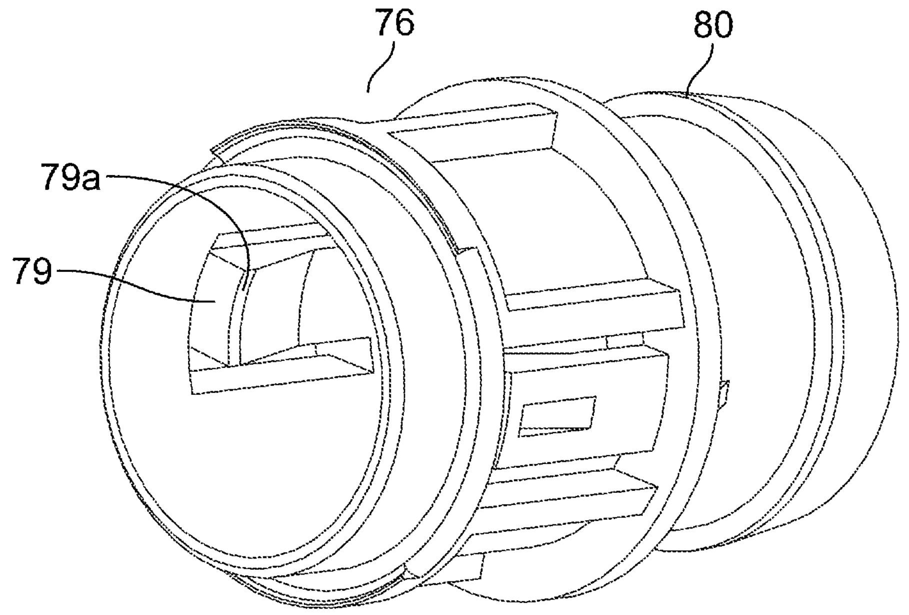
FIGS. 6A and 6B show different perspective views of the one possible design of the actuator sleeve of the present disclosure.
Figure 6B:
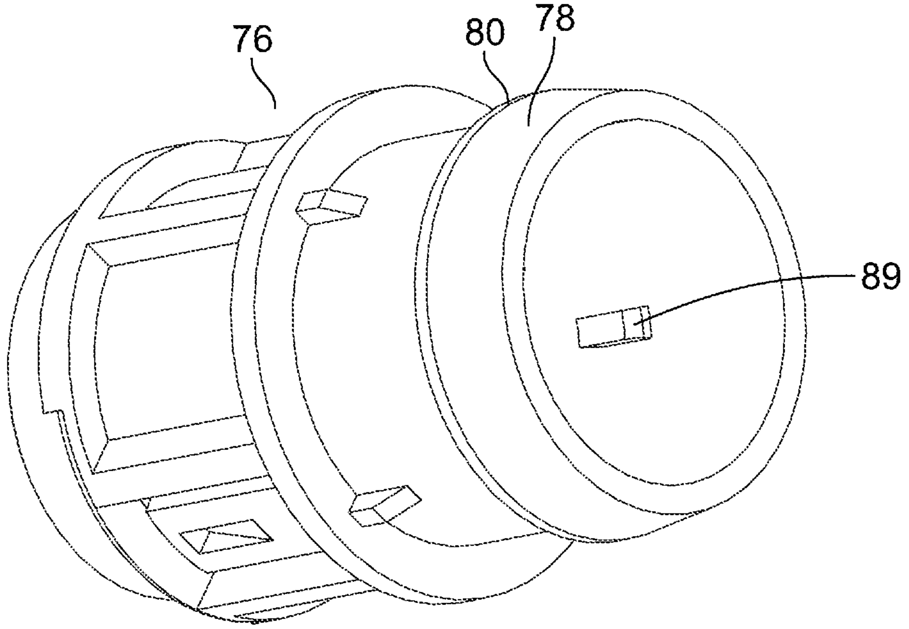
Figure 11:
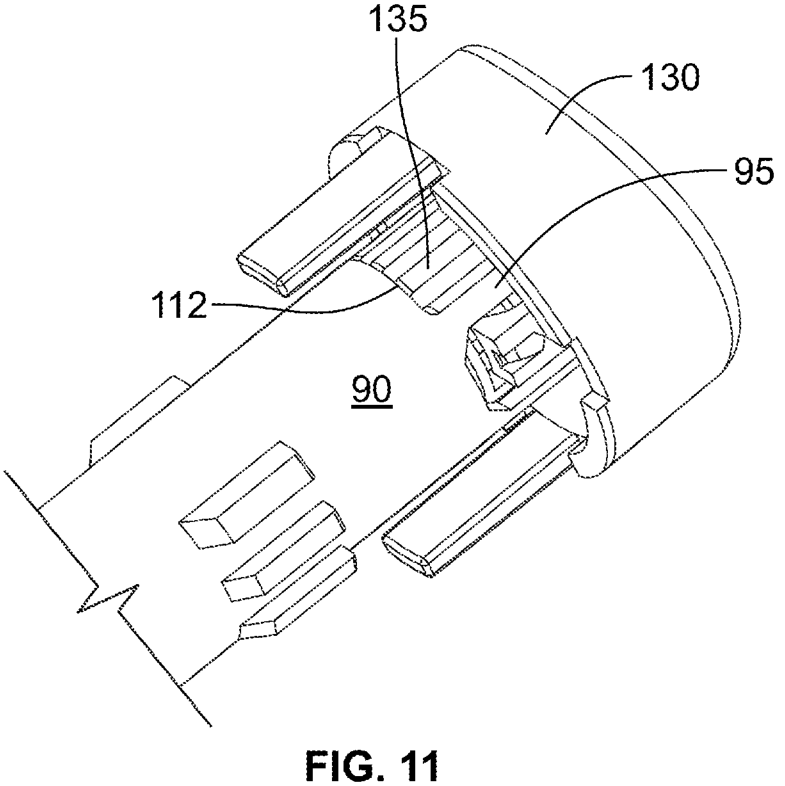
FIG. 11 shows a perspective view of the direct engagement of the activator of FIG. 9 with the distal end of the actuator of FIG. 7B of one possible design of the locking ring of the present disclosure.

The actuator 90 is also provided with one or more splines 93 that extend radially outward from an outer surface of the actuator. These splines cooperatively engage with corresponding splines 205 inside locking ring 200 (see FIG. 5) such that the locking ring and the actuator are rotationally fixed to each other, but axially slidable with each other. Stop elements 95 have a distally directed ledge 95*a* that directly engage with an inside surface of activator 130 (see FIGS. 8 & 11). The actuator 90 is further arranged with cut-outs 114, FIG. 7A, defining the stop elements 95 and having contact surfaces 112 that directly engage corresponding contact surfaces 135 that project proximally from inside activator 130 (see FIG. 11).

Figure 12:
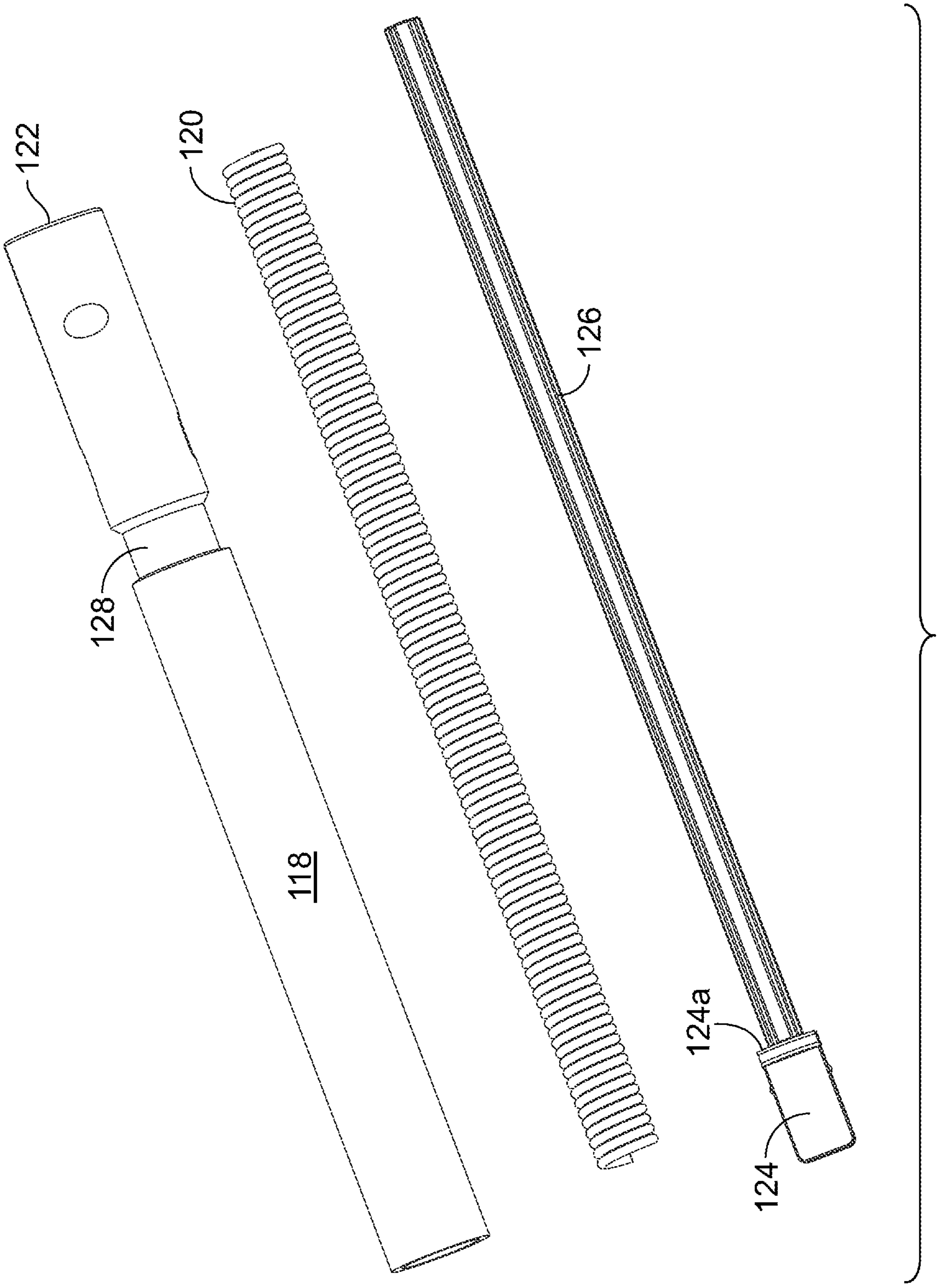
FIG. 12 shows a perspective view of one possible design of the assembly of the plunger rod, drive spring and guide rod of the present disclosure.

The power unit 64 further also has a plunger rod 118 arranged to act on the stopper 28 of the medicament container 26, FIGS. 2 & 12. A drive spring 120 that in the embodiment shown is a compression spring is arranged inside the plunger rod 118 between a proximal wall 122 of the plunger rod 118 and a proximally directed support surface of generally radially directed ledge 124*a* of distal end 124 of an elongated guide rod 126, which is extending through the drive spring 120. The ledge 124*a* acts as a bearing surface for the distal end of drive spring 120 and the distal end of the guide rod 126 is configured with a size and shape to fit into and through opening 99 in the distal end of actuator 90. The plunger rod 118 is arranged with a number of recesses that in the embodiment shown is a circumferential groove 128 with a certain width, wherein the annular inwardly directed ledge 110 of the actuator 90 and like radial inwardly directed ledges of the holding element 66 fit into the groove 128, FIG. 4. It is to be understood that the groove 128 may be replaced with a number of discrete recesses or cut-outs.

Figure 10:
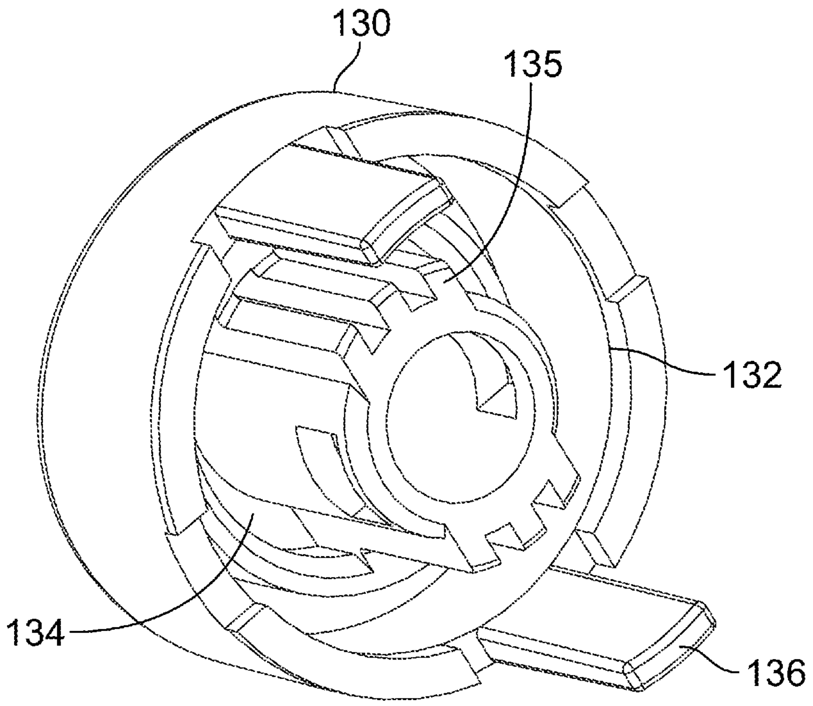
FIG. 10 shows a perspective view of one possible design of the activator as a dose button of the present disclosure.

A manually operated activator 130 (FIG. 10), e.g. a push button, has a distal portion protruding distally from the distal housing part 18 through the central passage of the housing. In the embodiment shown, the activator 130 comprises a generally tubular body 132 provided with a transversal end wall 134. A proximally directed edge of the tubular body 132 is arranged with proximally directed tongues 136, which tongues 136 are flexible in a generally radial direction. These tongues are to interact with inclined surfaces on the inner surface of the distal housing part 18 to prevent rotation of the activator relative to the outer housing 11.

The device further has a sleeve spring 154, coaxially arranged on the actuator sleeve 76 and on the locking ring 200. The annular proximal end of the sleeve spring 154 is arranged to rest on the second annular ring 84 of the actuator sleeve 76 and the annular distal end of the sleeve spring 154 is arranged resting on the proximal surfaces of the stop ledge 207 of the locking ring 200, FIGS. 3 & 4.

The dose delivery mechanism and the medicament delivery device of the present disclosure as just described is intended to function as follows. When the power unit 64 is to be assembled, the guide rod 126 is pushed into the actuator 90 from the proximal end until the distal end 124 of the guide rod 126 is snapped into opening 99 of the actuator 90. The locking ring 200 and actuator sleeve 76 with the sleeve spring 154 biased in between them is pushed onto the actuator 90. In this position the sleeve spring 154 is tensioned and the tongues 94 of the actuator 90 may flex in the generally radial direction. The drive spring 120 is then entered into the plunger rod 118 and the drive spring 120 and plunger rod 118 are pushed into the actuator 90 from the proximal direction, flexing the tongues 94 in the radial direction until the ledges 110 of the tongues 94 enter the annular groove 128, at the same time tensioning the drive spring 120.

The holding element 66 is pushed onto the plunger rod 118 from the proximal direction until the ledges of the holding element 66 also engage with the annular groove 128 of the plunger rod 118 and are positioned radially inwards of the tongues 94 of the actuator 90. Then the actuator sleeve 76 is pushed in the proximal direction onto the actuator 90, thereby preventing the ledges 110 of the tongues 94 of the actuator 90 as well as the ledges of the holding element 66 from escaping the annular groove 128 of the plunger rod 118. This assembly is then pushed into the distal housing part 18 from the proximal direction. The activator unit 130 is then pushed inside the distal housing part from the distal direction.

When the device is to be used, a medicament container 26 is placed in the container holder 52 and the assembly is placed in the proximal housing part 16. The distal housing part 18 with the power unit 64 is then interconnected and locked to the proximal housing part by the attachment elements 20. Further, the inwardly directed ledges 62 at the distal end of the medicament container holder 52 engage with the annular ledge 70 of the holding element 66, interconnecting them. The device is now ready to use. The distal part of the medicament delivery member guard 34 will surround the actuator sleeve 76 wherein the inclined tongues 48 will pass the ledge 80 providing an axial lock in the longitudinal direction of between the medicament delivery member guard 34 and the actuator sleeve 76. A distal end surface of the medicament delivery member guard 34 is in contact with the first annular ring 82.

When the medicament delivery device is to be used to deliver a dose of medicament, the protective cap 11*a* must first be removed from the proximal end of the outer housing 11, thus allowing the proximal end of the medicament delivery member guard 34 to be pressed against a dose delivery site. Now the medicament delivery device 10, apart from the stationary medicament delivery member guard 34 and the inter-connected actuator sleeve 76, is moved in the proximal direction until the distal end of the actuator sleeve 76 comes in contact with a central wall located inside of the distal housing part 18, wherein the movement is stopped.

The movement of the actuator 90 in relation to the actuator sleeve 76 has caused the band-shaped part 98 to protrude to some extent out of the proximal end of the actuator sleeve, setting the power unit in a first activation state. The user may now press on the activator or button 130 in the proximal direction whereby the contact surfaces 135 transfer the axial force and motion directly to the corresponding contact surfaces 112 on the distal end of the actuator 90. Because of the engagement of the actuator 90 with its ledges 110 in the annular groove 128 of the plunger rod 118, the axial movement activator 130 will also cause the same axial movement of the actuator 90 in the proximal direction. This movement will cause the band-shaped part 98 to be moved completely out of the actuator sleeve 76, and because of the resilient properties of the tongues 94 of the actuator 90, the ledges 110 will move radially outward out of the annular groove 128 of the plunger rod 118, thereby releasing the plunger rod 118, which is due to that both activation states have been set.

If for instance the medicament delivery device 10 would be removed from the dose delivery site, then the first activation state is removed. If now the activator 130 is pressed, the plunger rod 118 together with the actuator 90 will move proximally in relation to the actuator sleeve 76 to the second activation state, but because the actuator sleeve 76 has not been pushed distally by the medicament delivery member guard 34, the first activation state is not set and the plunger rod 118 will not be released.

Due to the force of the drive spring 120, the plunger rod 118 is urged in the proximal direction. Since the ledges 74 of the holding element 66 are still in the annular groove 128 and the holding element 66 is connected to the medicament container holder 52, the medicament container holder 52 and the medicament container 26 with its medicament delivery member 30 will be moved in the proximal direction, when the plunger rod 118 is moved in the proximal direction, causing a penetration of the medicament delivery member 30 into the tissue of the patient. The movement of the medicament container holder 52 and the medicament container 26 is stopped when the proximally directed surfaces surrounding the neck portion 26*a* abut a ledge on the inner surface of the medicament delivery member guard 34. It may also be that the force of the drive spring 120 will urge the plunger rod 118 in the proximal direction with such a force that the ledges of the holding element are forced out of the annular groove 128. However, since the plunger rod 118 is acting on the stopper 28 and due to the incompressibility of the medicament inside the medicament container 26 as well as the small passage in the medicament delivery member 30, the medicament container 26 with its container holder 52 will be moved in the proximal direction causing a penetration of the medicament delivery member 30 into the tissue of the patient.

The plunger rod 118 is urged further in the proximal direction wherein the ledges of the holding element 66 will be forced out of engagement with the annular groove 128 due to the flexing properties of the tongues 72 of the holding member. The plunger rod 118 will now act on the stopper 28 inside the medicament container 26, whereby a dose of medicament will be expelled through the medicament delivery member 30. When the plunger rod 118 has come to its most proximal position with the stopper 28 at the proximal end of the medicament container 26, an end-of-dose signal mechanism will be activated. This signal is caused when the outward facing locking nibs 102 of flexible arms 100 of the actuator 90 engage the terminal end 203 of a proximally extending first leg 208 of locking ring 200 (see FIG. 8). The sleeve spring 154 causes the locking ring 200 to move axially in the distal direction which in turn exposes the nibs 102 and allows flexible arms 100 to flex radially outward generating the signal that is perceived by a user of the medicament delivery device as a tactile or audible signal or both.

Figure 9:
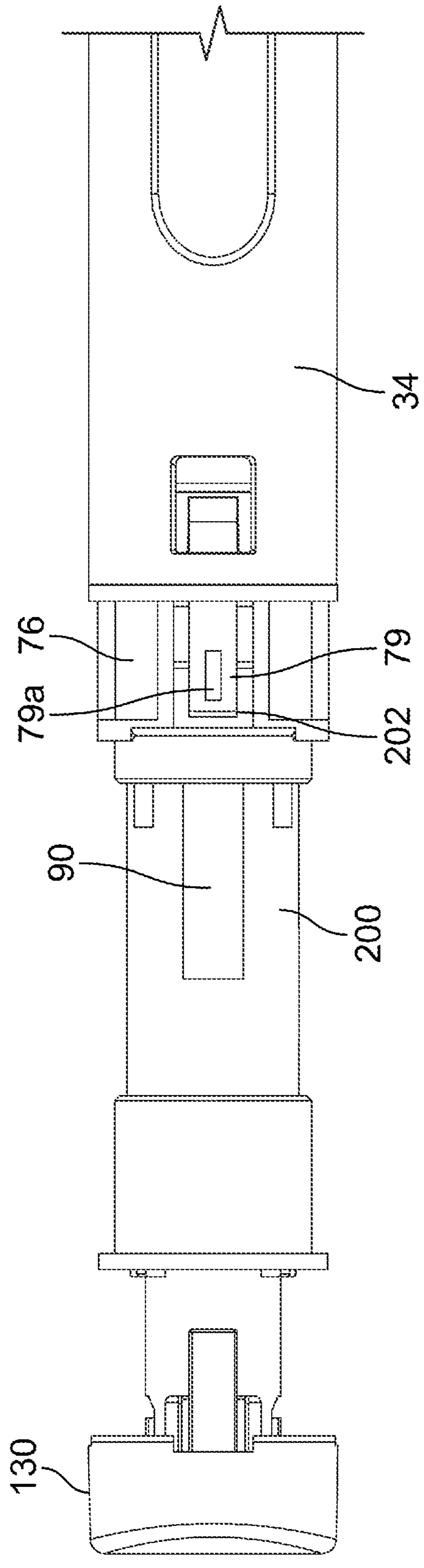
FIG. 9 shows the engagement of the locking ring of FIG. 5 with the radially inward directed protrusion of activator sleeve of FIG. 6A at an end of dose delivery position.

Once the end-of-dose delivery signal is generated, the user may now remove the medicament delivery device from the dose delivery site. This will cause actuator sleeve 76 and the medicament delivery member guard 34 to be moved in the proximal direction due to the force from the sleeve spring 154 acting on the actuator sleeve 76 and because of the connection between the actuator sleeve 76 and the medicament delivery member guard 34, which movement will cause the medicament delivery member 30 to be shielded. Once the guard 34 reaches its proximally extended position, the guard 34 will locked because when the actuator sleeve 76 is moved in the proximal direction by the sleeve spring 154, the radially inward directed protrusion 79*a* of flexible finger 79 of the actuator sleeve 76 will then operatively engage with and abut the terminal end surface 202 of the second leg 206 of the locking ring 200. This abutment between 202 and 79*a* will prevent axial movement of the guard 34 and actuator sleeve 76 in the distal direction (FIG. 9). This lock feature caused by the abutment of protrusion 79*a* with end surface 202 will prevent any attempt to push the medicament delivery member guard 34 in the distal direction thus preventing exposure of delivery member 30. The device is now safe to discard.

Figure 13:
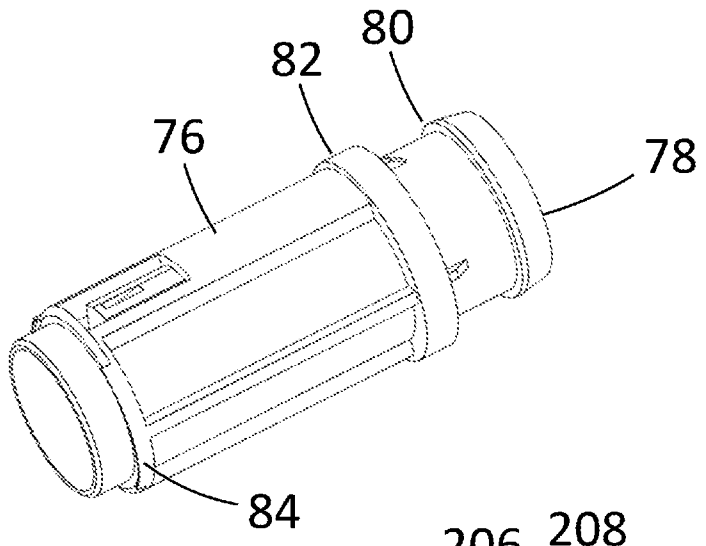
FIG. 13 shows a perspective view of an alternative actuator sleeve.
Figure 14:
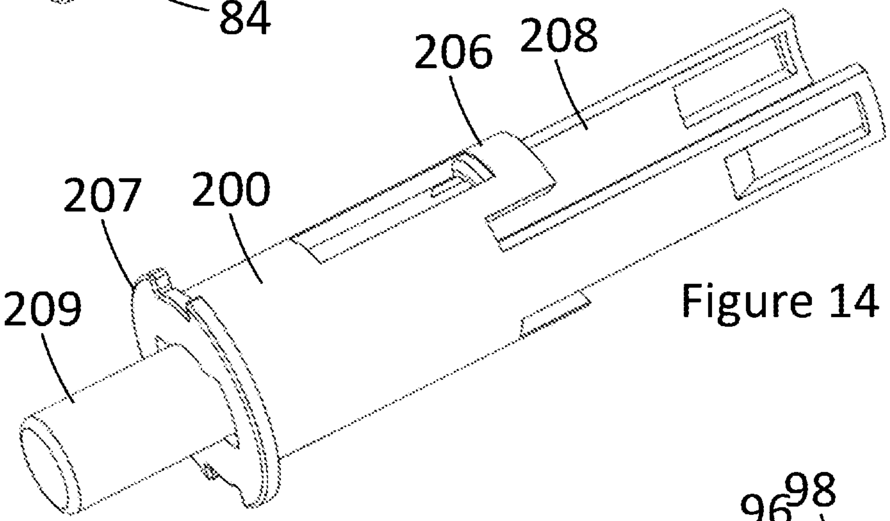
FIG. 14 shows a perspective view of an alternative locking ring.
Figure 15:
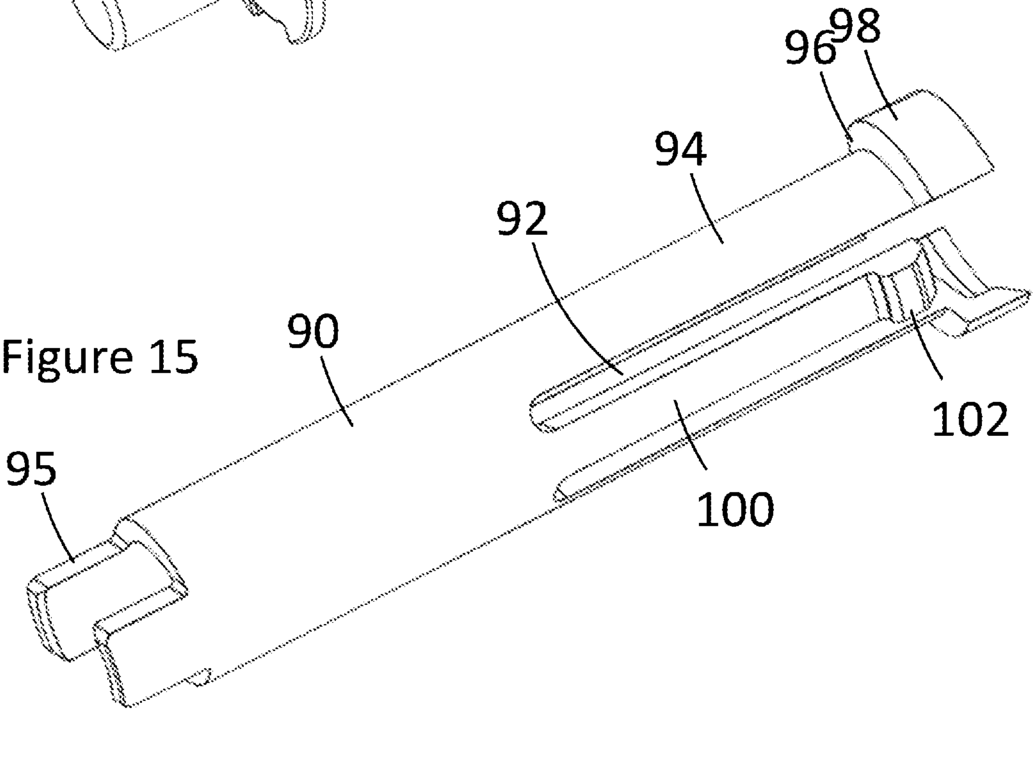
FIG. 15 shows a perspective view of an alternative actuator.

Variations can also be made in the shape of the actuator sleeve 76, the locking ring 200 and the actuator 90. For example, FIGS. 13, 14 and 15 show a differently shaped actuator sleeve 76, locking ring 200 and actuator 90 respectively. Like features are indicated by like reference numerals. Some non-essential features are not present; for example, the actuator 90 in FIG. 15 does not have splines 93. Another difference in this structure is that the locking ring 200 comprises an end cap 209. This can receive the drive spring 120. This is therefore an example of a design in which an end click can be generated using the force of both the sleeve spring 154 and the drive spring 120.

Various structures can be used beyond those described above. For example, other structures are possible to lock structures such as the actuator and the locking ring rotationally whilst allowing axial movement relative to one another. For example, the inner surface of the locking ring can describe a square in the transverse plane, with a corresponding square shape for the structure of the actuator, as a replacement for splines 93. The notch in stop ledge 207 in FIG. 14 can also provide a rotational lock without an axial lock, as can the nib 102 on the actuator 90.

Figure 16:
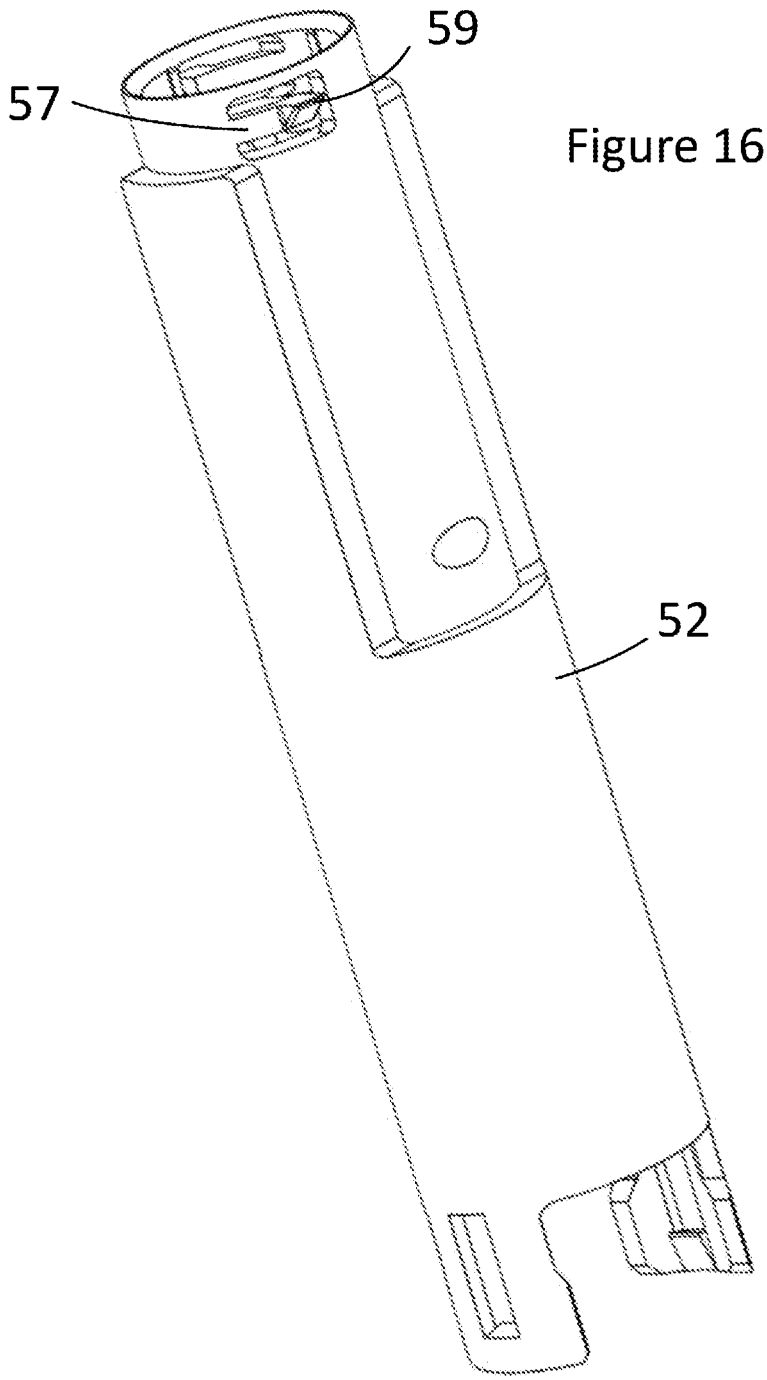
FIG. 16 shows a perspective view of an alternative medicament container holder.

Finally, FIG. 16 shows an alternative medicament container holder 52. In particular, the medicament container holder comprises a flexible arm 57 extending circumferentially relative to the longitudinal axis. The flexible arm comprises a protrusion 59. The protrusion is outwardly directed (i.e. away from the longitudinal axis), although in other embodiments it could be inwardly directed. This feature can help hold the cap 11*a* on the device, and/or can help increase the friction between the cap and the medicament container holder to make it harder to remove the cap. Two arms are shown, each with one protrusion, though other numbers of arms or of protrusions could be provided. In this example, the flexible arm extends in a cut-out in the tubular body of the medicament container holder.

It is to be understood that the embodiments described above and shown in the drawings are to be regarded as a non-limiting example of the present disclosure and that they may be modified in many ways within the scope of the patent claims.

I claim:

1. A dose delivery mechanism comprising:

a plunger rod comprising a groove on an outside surface;

an actuator having a holding ledge engaged with the groove such that the plunger rod is held in a first axial position, where disengagement of the holding ledge from the groove allows the plunger rod to move to a second axial position;

an actuator sleeve biased proximally by a sleeve spring and movable in both a distal and proximal direction, where the actuator sleeve has a flexible finger;

an activator movable in a proximal direction and directly engaged with the actuator such that axial movement of the activator moves the actuator proximally relative to the actuator sleeve; and a locking ring slidably engaged and rotationally fixed with an outside surface of the actuator and engaged with the sleeve spring, where the locking ring has a proximally extending first leg that abuts a flexible arm of the actuator when the plunger rod is in the second axial position.

2. The dose delivery mechanism of claim 1, wherein relative movement between the first leg and the flexible arm generates an end of medicament notification through a tactile or audible signal.

3. The dose delivery mechanism of claim 1, wherein the locking ring has a proximally extending second leg that abuts the flexible finger after the plunger rod has moved to the second axial position to form an axial lock that prevents axial movement of the actuator sleeve in a distal direction.

4. The dose delivery mechanism of claim 3, further comprising a medicament delivery guard axially fixed to the actuator sleeve.

5. The dose delivery mechanism of claim 4, where the medicament delivery guard is configured to have a first position, a second position and a third position relative to the activator.

6. The dose delivery mechanism of claim 4, wherein the flexible finger of the actuator sleeve comprises a radial inward directed protrusion that abuts a proximal facing end surface of the second leg when the plunger rod is in the second axial position such that the medicament delivery guard is prevented from axial movement in the distal direction relative to the actuator.

7. The dose delivery mechanism of claim 4 further comprising a holding element releasably engaged with the groove when the plunger rod is in the first axial position and disengaged from the groove when the plunger rod is in the second axial position.

8. The dose delivery mechanism of claim 7 further comprising a medicament container holder axially fixed to the holding element and slidably positioned inside the medicament delivery guard.

9. The dose delivery mechanism of claim 4, wherein axial movement of the medicament delivery guard in a distal direction causes the actuator sleeve to move distally to an activation state.

10. The dose delivery mechanism of claim 9, wherein axial movement of the activator in a proximal direction when the actuator sleeve is in the activation state causes the actuator to move relative to the actuator sleeve such that the holding ledge will disengage from the groove.

11. The dose delivery mechanism of claim 1, wherein an inside surface of the locking ring has a first set of splines that are slidably engaged with a second set of splines on the outside surface of the actuator that prevent relative rotation of the locking ring.

12. The dose delivery mechanism claim 1, wherein the plunger rod is hollow.

13. The dose delivery mechanism of claim 12, wherein a drive spring is located inside the plunger rod.

14. The dose delivery mechanism of claim 13 further comprising a guide rod positioned inside of the drive spring, where the guide rod has a distal end portion configured to slidably engage a distal end of the actuator such that the guide rod is rotationally fixed relative to the actuator.

15. The dose delivery mechanism of claim 14, wherein the drive spring is biased between the distal end portion of the guide rod and a proximal interior wall of the plunger rod when the plunger rod is in the first axial position.

16. The dose delivery mechanism of claim 1, wherein the activator comprises a tongue that is biased radially outward relative to the plunger rod, and wherein the holding ledge is located at a proximal end of the tongue.

17. The dose delivery mechanism of claim 1, wherein the actuator sleeve is arranged slidable in relation to the actuator.

18. The dose delivery mechanism of claim 1, wherein a distal end surface of the locking ring is engaged with a distal end of the sleeve spring.

19. The dose delivery mechanism of claim 1, wherein the holding ledge is an annular inwardly directed ledge, and wherein the holding ledge is arranged in the groove prior to use of the dose delivery mechanism to deliver a medicament.

20. A medicament delivery device comprising:

a housing, where the dose delivery mechanism of claim 1 is positioned within the housing;

a medicament container operatively connected to the dose delivery mechanism; and a medicament delivery member connected to the medicament container.

* * * * *